United States Patent [19]

Flowers

[11] Patent Number: 5,733,264
[45] Date of Patent: Mar. 31, 1998

[54] SHIELDABLE SYRINGE ASSEMBLY

[75] Inventor: Richard A. Flowers, Garfield, N.J.

[73] Assignee: Becton, Dickinson and Company, Franklin Lakes, N.J.

[21] Appl. No.: 787,407

[22] Filed: Jan. 22, 1997

[51] Int. Cl.$^6$ .................................................. A61M 5/32
[52] U.S. Cl. ...................................... 604/198; 604/263
[58] Field of Search ............................ 604/198, 110, 604/192, 187, 263, 195

[56] References Cited

U.S. PATENT DOCUMENTS

| | | |
|---|---|---|
| 2,801,741 | 8/1957 | Harkness et al. . |
| 4,285,105 | 8/1981 | Kirkpatrick .................. 24/201 |
| 4,631,057 | 12/1986 | Mitchell ...................... 604/198 |
| 4,723,943 | 2/1988 | Spencer ...................... 604/198 |
| 4,737,144 | 4/1988 | Choksi ........................ 604/198 |
| 4,743,233 | 5/1988 | Schneider .................... 604/192 |
| 4,747,837 | 5/1988 | Hauck ......................... 604/198 |
| 4,801,295 | 1/1989 | Spencer ...................... 604/198 |
| 4,840,185 | 6/1989 | Hernandez .................... 128/763 |
| 4,871,355 | 10/1989 | Kikkawa ...................... 604/198 |
| 4,900,310 | 2/1990 | Ogle, II ...................... 604/198 |
| 4,927,018 | 5/1990 | Yang et al. .................. 206/365 |
| 4,947,863 | 8/1990 | Haber et al. ................. 128/764 |
| 4,994,045 | 2/1991 | Ranford ...................... 604/198 |
| 4,998,920 | 3/1991 | Johnson ...................... 604/198 |
| 4,998,924 | 3/1991 | Ranford ...................... 604/798 |
| 5,019,051 | 5/1991 | Hake .......................... 604/198 |
| 5,024,660 | 6/1991 | McNaughton ................... 604/110 |
| 5,045,066 | 9/1991 | Scheuble et al. .............. 604/198 |
| 5,053,018 | 10/1991 | Talonn et al. ................ 604/198 |
| 5,057,086 | 10/1991 | Dillard, III et al. .......... 604/195 |
| 5,057,087 | 10/1991 | Harmon ....................... 604/198 |
| 5,059,185 | 10/1991 | Ryan ......................... 604/198 |
| 5,067,945 | 11/1991 | Ryan et al. .................. 604/198 |
| 5,137,521 | 8/1992 | Wilkins ...................... 604/198 |
| 5,141,500 | 8/1992 | Hake .......................... 604/198 |
| 5,147,303 | 9/1992 | Martin ....................... 604/110 |
| 5,169,392 | 12/1992 | Ranford et al. ............... 604/198 |
| 5,188,614 | 2/1993 | Hart .......................... 604/197 |
| 5,197,953 | 3/1993 | Colonna ...................... 604/110 |
| 5,217,437 | 6/1993 | Talonn et al. ................ 604/198 |
| 5,415,645 | 5/1995 | Friend et al. ............... 604/198 X |
| 5,429,612 | 7/1995 | Berthier ..................... 604/198 |
| 5,549,558 | 8/1996 | Martin ....................... 604/110 |
| 5,562,624 | 10/1996 | Righi et al. ................ 604/263 X |
| 5,582,597 | 12/1996 | Brimhall et al. ............. 604/263 X |

*Primary Examiner*—John D. Yasko
*Attorney, Agent, or Firm*—John L. Voellmicke

[57] ABSTRACT

A shieldable syringe assembly includes a syringe barrel having opposed proximal and distal ends and an annular groove extending inwardly near said distal end. A locking collar is mounted on said distal end of said syringe barrel and includes a plurality of barbs engaged in the groove. Outer portions of the locking collar aligned with the barbs define a collet that is inwardly deformable. A rigid safety shield is telescoped over the locking collar and the syringe barrel. The safety shield can be slid from a proximal position to a distal position. Interior portions of the safety shield are configured to lockingly engage the collet when the safety shield is in the distal position. The collet engaging portions of the safety shield deform the collet inwardly into tight gripping engagement in the groove on the syringe barrel for preventing separation of the safety shield and the locking collar from the syringe barrel.

11 Claims, 7 Drawing Sheets

SHIELDABLE SYRINGE ASSEMBLY

BACKGROUND OF THE INVENTION

1. Field of the Invention

The subject invention relates to a shield for a hypodermic syringe to help prevent accidental contact with a needle cannula.

2. Description of the Prior Art

The prior art hypodermic syringe includes a syringe barrel having opposed proximal and distal ends and a tubular wall extending therebetween to define a fluid receiving chamber. The distal end of the syringe barrel is partly closed and terminates in a short distally extending tip having a passage that communicates with the fluid receiving chamber of the barrel. The proximal end of the barrel is widely open and receives a plunger in sliding fluid tight engagement. Distal movement of the plunger expels fluid from the chamber through the passage in the tip of the syringe barrel. Proximal movement of the plunger will draw fluid into the chamber.

The distal end of many hypodermic syringes is further characterized by a cylindrical luer collar concentrically surrounding the tip. Internal surface regions of the luer collar are provided with an array of threads.

The prior art hypodermic syringe may further be provided with a needle assembly which includes a needle cannula and a needle hub. The needle cannula includes a proximal end, a sharp distal end and a lumen extending therebetween. The proximal end of the prior art needle cannula is securely embedded in the needle hub. The hub of the prior art needle assembly can be threadedly engaged with the luer collar to place the lumen through the needle cannula in communication with the passage through the tip of the hypodermic syringe.

Accidental sticks with the distal tip of a needle cannula can be painful and can transmit disease. As a result, most prior art hypodermic syringes include shields for protectively surrounding at least the sharp distal end of the needle cannula. A safety shield for a hypodermic syringe should be easy to use and should avoid interference with normal usage of the hypodermic syringe. Furthermore, it may be desirable to prevent re-exposure of the shielded needle cannula to prevent unauthorized reuse of the hypodermic syringe.

A prior art safety shield is illustrated in U.S. Pat. No. 5,385,555. The shield shown in U.S. Pat. No. 5,385,555 is a rigid tubular structure having opposed proximal and distal ends and a length approximately equal to the length of the syringe barrel. The shield is telescoped over the syringe barrel and is slidably movable from a proximal position where the needle cannula is exposed and ready for use, to a distal position where the shield safely surrounds the needle cannula. The proximal end of the shield and the proximal end of the syringe barrel include structure for releasably retaining the shield in its proximal position prior to and during use of the hypodermic syringe. Locking structure also is provided for permanently locking the safety shield in its distal position surrounding the needle cannula.

The locking structure for locking the safety shield in its distal position includes a locking collar disposed in surrounding relationship to the cylindrical luer collar. The locking collar is provided with a plurality of barbs configured for permitting the locking collar to be slid proximally over the cylindrical luer collar. However, the barbs will bite into the plastic of the cylindrical luer collar in response to distally directed forces. The locking collar further includes a locking wall at the proximal end of the locking collar. The locking wall is a generally frustoconical skirt and includes a minor dimension at the proximal end of the locking collar which is greater than the outside diameter of the syringe barrel. The locking wall flares outwardly at more distal positions thereon, and the extreme distal end of the locking wall is deflectable inwardly. The proximal end of the safety shield includes a plurality of stop blocks which define an inside diameter less than the minor diameter of the locking wall on the locking collar. Interior regions of the safety shield further include a plurality of locking ramps spaced proximally from the stop blocks. Interior portions of the safety shield between the stop blocks and the ramp are cylindrical.

The safety shield of U.S. Pat. No. 5,385,555 is used by sliding the safety shield distally relative to the syringe barrel. After sufficient distal movement, the ramps on the interior of the safety shield will engage the locking wall of the locking collar. The ramps will generate inward deflection of the locking wall so that the safety shield can advance further in a distal direction. After sufficient distal movement of the safety shield, the ramps clear the locking wall of the locking collar, thereby permitting the locking wall to resiliently return toward an undeflected condition. Further distal movement of the safety shield will drive the stop locks into the proximal end of the locking wall on the locking collar. Thus, the safety shield is effectively locked in its extended distal position in surrounding relationship to the used needle cannula. The exertion of proximal forces on the safety shield in an effort to reuse the needle cannula will cause the distal end of the ramps in the safety shield to engage the major diameter end of the locking wall. The frustoconical skirt-like locking wall will not deflect in response to proximal forces, and the locking collar will merely be driven into the shoulder of the syringe barrel surrounding the luer collar. Attempts to remove the safety shield in a distal direction will urge the stop blocks into the proximal end of the locking collar and will drive the barbs of the locking collar into the plastic of the luer collar.

SUMMARY OF THE INVENTION

The subject invention is directed to a shieldable hypodermic syringe assembly. The assembly includes a syringe barrel having opposed proximal and distal ends and a tubular side wall extending therebetween to define a fluid receiving chamber within the barrel. A tip extends distally at the distal end of the barrel and includes a fluid passage extending axially therethrough. A luer collar also extends distally at the distal end of the syringe barrel and is in surrounding concentric relationship to the tip. The interior of the luer collar includes an array of threads for threaded engagement with a needle hub as in the prior art.

The luer collar preferably defines a smaller outside diameter than the tubular side wall of the syringe barrel. Thus, a shoulder is defined at the interface of the luer collar and the tubular side wall of the syringe barrel. Additionally, an annular groove may be defined at the proximal end of the luer collar substantially adjacent the annular shoulder. The annular groove may be approximately V-shape in cross-section and may be defined by two intersecting conically generating surfaces.

The safety shield assembly of the subject invention includes a short generally tubular locking collar having opposed proximal and distal ends and a length approximately equal to the axial length of the luer collar. The distal end of the locking collar may be substantially cylindrical and may define an inside diameter dimensioned for slidable engagement over the luer collar. The proximal end of the locking collar includes an inside surface characterized by a plurality of locking barbs. Each barb includes a radially aligned distal wall and a tapered proximal wall. The inside diameter defined by opposed barbs is approximately equal to the minimum diameter defined within the annular groove around the outside of the luer collar.

The exterior of the proximal end of the locking collar defines a frustum-shaped collet with a minor outside diameter at the proximal end and a major outside diameter spaced distally from the proximal end. The minor outside diameter of the collet is larger than the outside diameter defined by the tubular side wall of the syringe barrel. The locking collar may further be provided with a plurality of axially extending slots extending a short distance from the proximal end. The slots are provided to enable resilient expansion and contraction of the collet during assembly to the syringe barrel.

The safety shield is a rigid tubular member having opposed proximal and distal ends and a length approximately equal to the length of the syringe barrel. The safety shield includes at least one lock block on the interior of the safety shield substantially at the distal end. The lock block defines an inside diameter slightly greater than the outside diameter of the tubular side wall of the syringe barrel, but less than the minor outside diameter of the collet at the proximal end of the locking collar. The interior of the safety shield includes a collet actuator distally of the stop block. The collet actuator may be a frustum-shaped or wedge-shaped interior surface region. The frustum-shaped or wedge-shaped region on the inside of the safety shield includes a minor inside diameter substantially adjacent the locking flange which is greater than the minor diameter of the collet on the locking collar.

The interior of the safety shield further includes pawls distally of and adjacent to the frustum or wedge shaped regions. The pawls define a minor inside diameter immediately adjacent the frustum or wedge shaped regions which is less than the major outside diameter of the collet at the proximal end of the locking collar. A safety cap may then be affixed over the distal end of the safety shield for further protection against accidental needle sticks.

The hypodermic syringe is used in the conventional manner. After use, the technician merely holds the distal end of the syringe barrel in one hand and the shield in the other hand. The shield is then slid distally along the syringe barrel. After sufficient movement, the tapered pawls on the safety shield will engage the collet on the locking collar. This ramped engagement will cause a slight inward deflection of the collet to permit further distal movement of the safety shield. After such further distal movement, the minor diameter end of the frustum-shaped collet actuator region in the safety shield will engage the collet on the locking collar. Wedging forces by the interengaged wedged members will drive the barbs at the proximal end of the locking collar into tighter gripping engagement with the groove in the luer collar, thereby positively preventing removal of the safety shield in the distal direction. Proximally directed forces on the safety shield in an effort to re-expose the used needle cannula will urge the radial aligned pawl surfaces into locking engagement with the distal end of the collet on the locking collar, thereby urging the proximal end of the locking collar into the shoulder of the syringe barrel. Thus, the safety shield is positively locked against movement in either the proximal or distal direction for preventing any unauthorized re-exposure of the used needle cannula.

DETAILED DESCRIPTION OF THE PREFERRED EMBODIMENT

Figure 1:
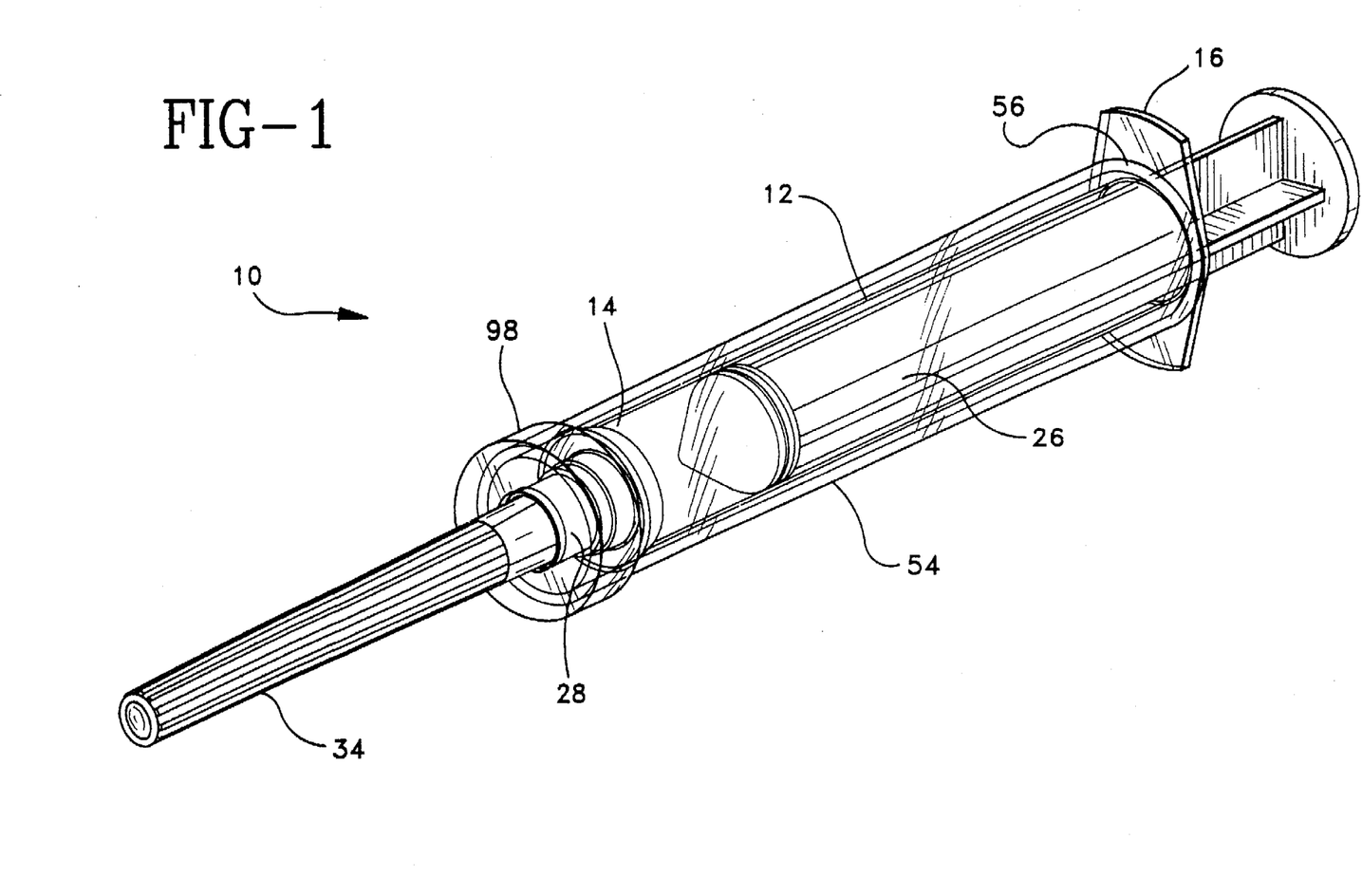
FIG. 1 is a perspective view of a hypodermic syringe with a safety shield in accordance with the present invention.
Figure 2:
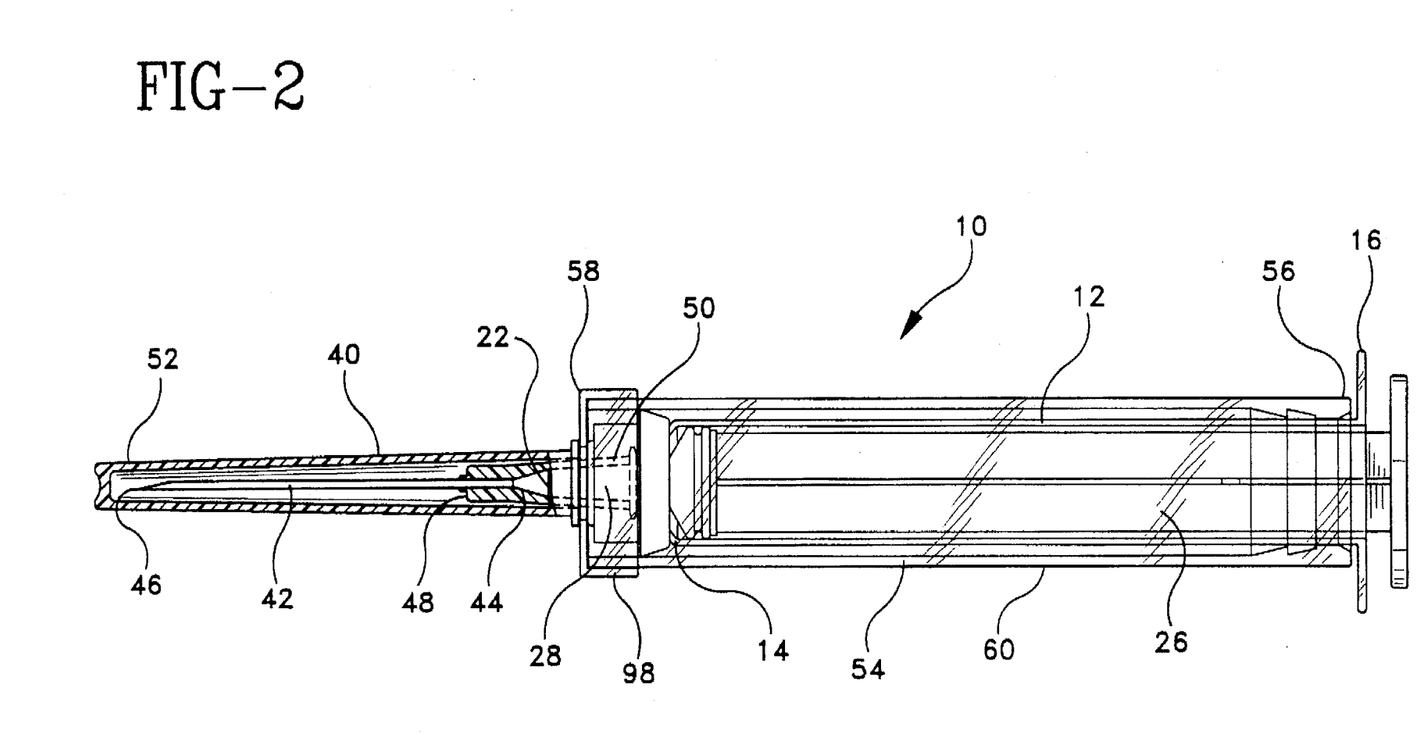
FIG. 2 is a side elevational view, partly in section, of the hypodermic syringe of FIG. 1
Figure 3:
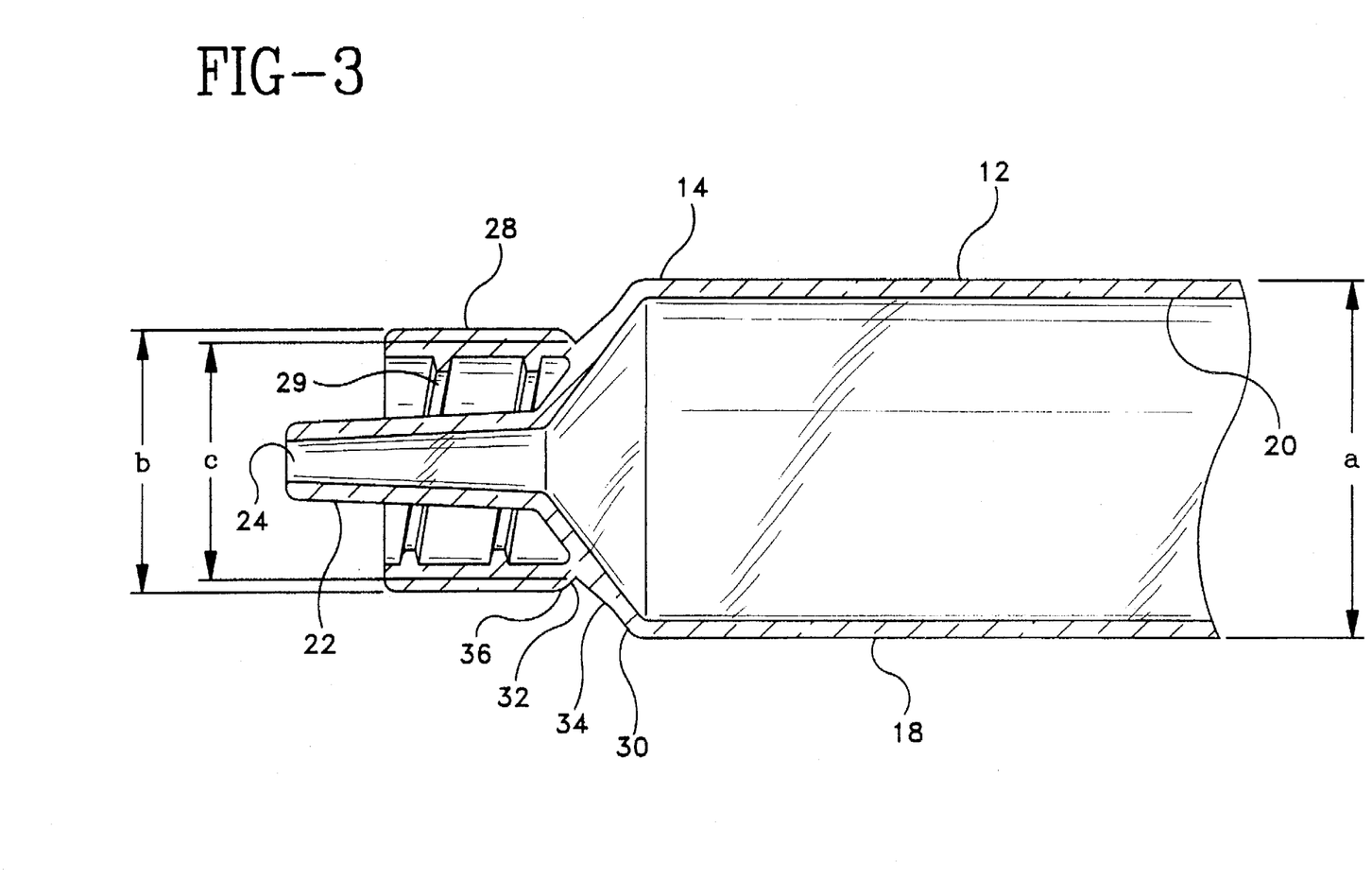
FIG. 3 is a cross-sectional view of the distal end of the hypodermic syringe barrel prior to mounting the safety shield assembly of the present invention.

A shieldable syringe assembly in accordance with the subject invention is identified generally by the numeral 10 in FIGS. 1 and 2. Hypodermic syringe 10 includes a generally cylindrical syringe barrel 12 having a partly closed distal end 14, a widely opened proximal end 16, and a cylindrical side wall 18 extending therebetween to define a fluid receiving chamber 20 therein. Cylindrical side wall 18 defines an outside diameter "a" as shown in FIG. 3. Hypodermic syringe 10 further includes a tapered tip 22 projecting distally from syringe barrel 12. Tip 22 includes a passage 24 extending therethrough and communicating with fluid receiving chamber 20. A plunger 26 is slidably received in chamber 20. Slidable movement of plunger 26 proximally from the condition shown in FIG. 2 will draw fluid through passage 24 in tip 22 and into chamber 20. Distal movement of plunger 26 will expel fluid from chamber 20 through passage 24 in tip 22. Syringe 12 further includes a luer collar 28 in surrounding relationship to tip 22. Luer collar 28 is provided with an array of internal threads 29 for threadedly receiving the hub of a needle assembly as explained further herein. Luer collar 28 defines an outside diameter "b" which is less than outside diameter "a" of cylindrical side wall 18 of syringe barrel 12. Thus, an annular shoulder 30 is defined between luer collar 28 and cylindrical side wall 18 of syringe barrel 12. Luer collar 28 is further characterized by an annular groove 32 substantially adjacent annular shoulder 30. Annular groove 32 is formed by two intersecting frustum surfaces, including a proximal frustum surface 34 and a distal frustum surface 36. The frustum surfaces 34 and 36 defining groove 32 intersect to define a minor outside diameter "c" which is less than outside diameter "b" for luer collar 28.

Hypodermic syringe assembly 10 is used with a needle assembly 40 having a needle cannula 42 with a proximal end 44, a distal end 46 preferably including a sharpened tip 47 and a lumen extending continuously therebetween. Proximal end 44 of needle cannula 42 is securely embedded in a hub 48. Hub 48 includes projections 50 which are dimensioned and configured for threaded engagement with luer collar 28. A safety cap 52 is telescoped over needle cannula 42 and is frictionally engaged on hub 48. Safety cap 52 is effective for preventing accidental sticks prior to initial usage of hypodermic syringe 10. Immediately prior to use, safety cap 52 may be removed and discarded.

Figure 4:
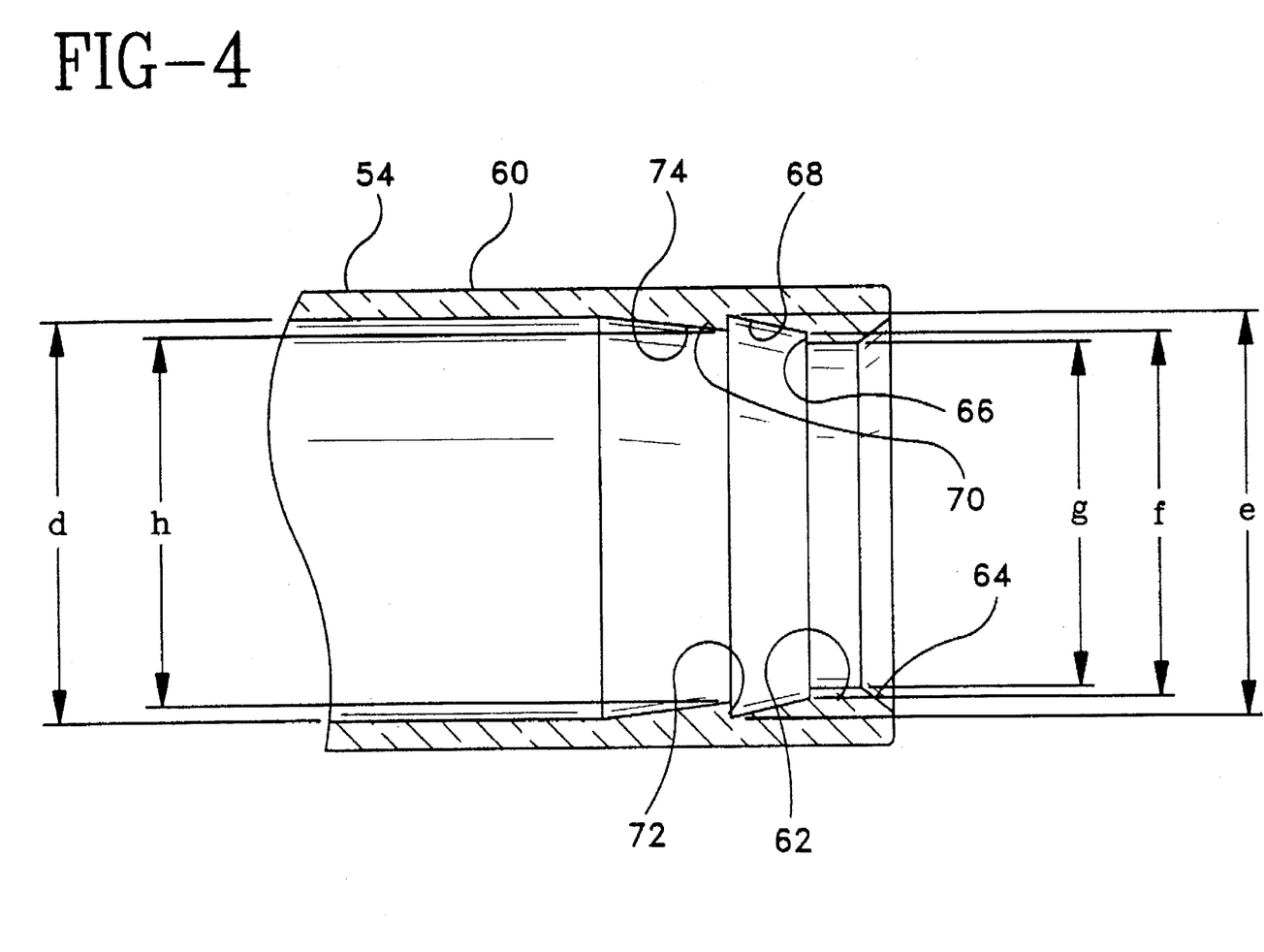
FIG. 4 is a cross-sectional view showing the proximal end of the safety shield assembly of the present invention.

Shieldable hypodermic syringe 10 further includes a rigid tubular safety shield 54 slidably telescoped over syringe barrel 10. Safety shield 54 includes a proximal end 56, a distal end 58 and a rigid tubular side wall 60 extending continuously therebetween. Tubular side wall 60 defines an inside diameter "d" along a major portion of the length of safety shield 54 extending proximally from distal end 58 thereof. Interior portions of safety shield 54 adjacent proximal end 56 include an inwardly directed locking shoulder 62 having a chamfered proximal face 64 and radially aligned distal locking face 66. Locking shoulder 62 defines an inside diameter "e" slightly greater than outside diameter "a" of syringe barrel. Thus, locking shoulder 62 of safety shield can be slid along syringe barrel 12. For ease of manufacture, the locking shoulder may have a plurality of circumferentially spaced discontinuities.

Interior portions of safety shield 54 distally of locking shoulder 62 define a frustum-shaped wedge surface 68 having a minor inside diameter "f" adjacent locking face 66 of locking shoulder 62 and a major inside diameter "g" at the distal extreme position on wedge surface 68.

Pawls 70 are defined distally of wedge surface 68 and include a radially aligned pawl face 72 defining the distal extreme of wedge surface 68 and a ramp face 74 distally of pawl face 72. The intersection of pawl face 72 and ramp face 74 defines an inside diameter "h" which is greater than minor inside diameter "f" of wedge surface 68. The distal end of ramp face 74 of pawl 70 intersects the cylindrical inner surface of safety shield 60 which continues to distal end 58. Again, for ease of manufacture, pawls 70 may align with the circumferential discontinuities in locking shoulder 62.

Figure 5:
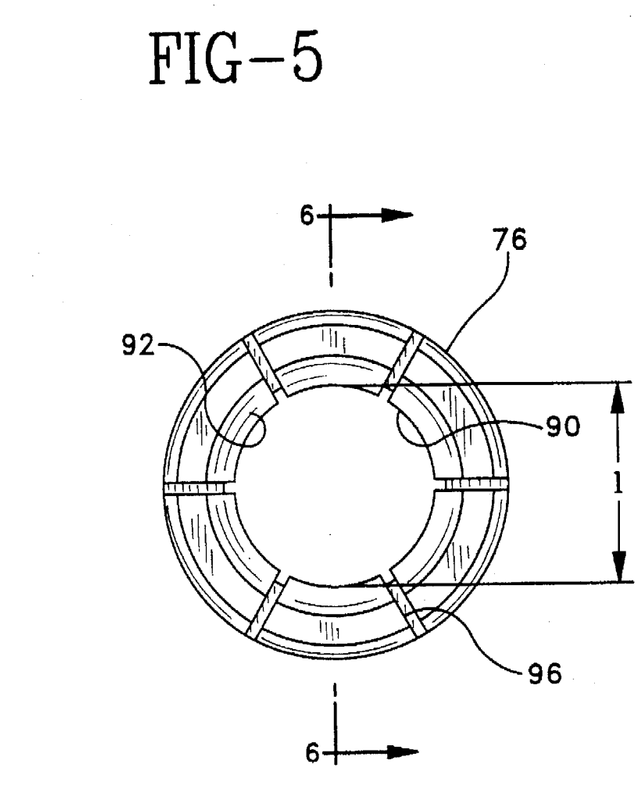
FIG. 5 is an end elevational view of the locking collar.
Figure 6:
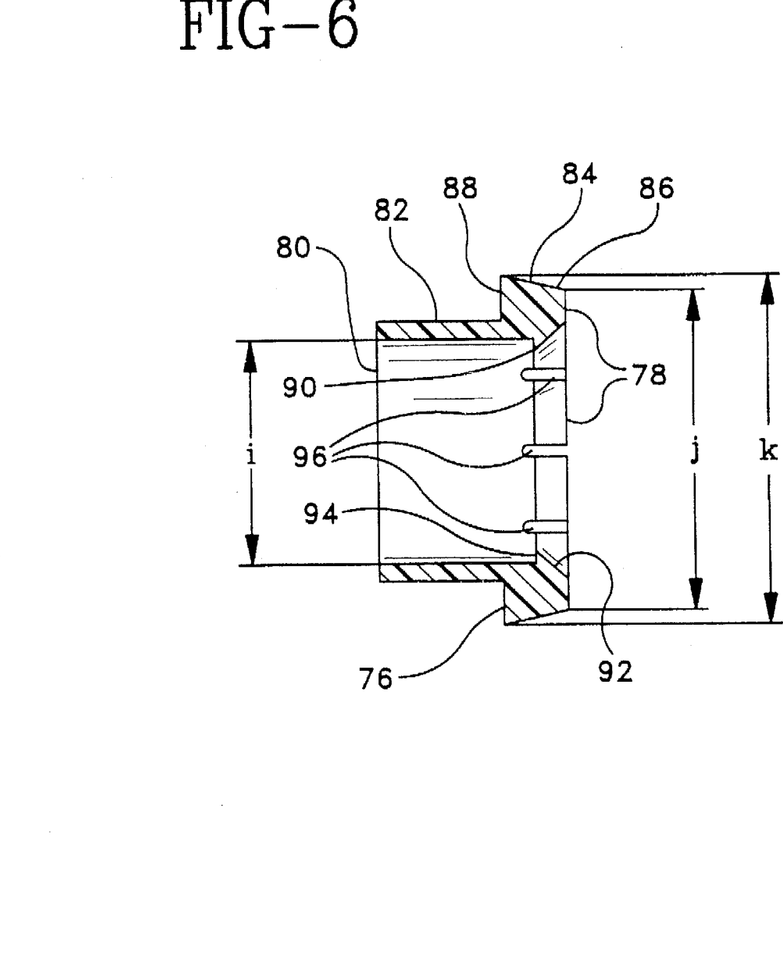
FIG. 6 is a cross-sectional view taken along lines 6—6 in FIG. 5.

Shieldable needle assembly 10 further includes a locking collar 76 having a proximal end 78, a distal end 80 and a generally tubular side wall 82, as shown in FIGS. 5 and 6. Side wall 82 preferably has substantially cylindrical inner and outer surfaces along a major portion of its length extending proximally from distal end 80. Interior surface regions of tubular side wall 82 adjacent distal end 80 define an inside diameter "i" which is preferably but not necessarily slightly greater than outside diameter "b" of luer collar 28.

Proximal end 78 of locking collar 76 defines a collet with an annular exterior wedge 84 having a frustum-shaped proximal face 86 and a radially aligned distal face 88. The extreme proximal end 78 of locking collar 76 defines an outside diameter "j" which is greater than the outside diameter "a" of cylindrical side wall 18 of syringe barrel 12 and greater than the inside diameter "e" of locking shoulder 62 on safety shield 54. The intersection of frustum-shaped exterior wall 86 and distal face 88 of exterior wedge 84 define an outside diameter "k" which is greater than the inside diameter "g" defined by the intersection of pawl face 72 and ramp face 74 of pawls 70 on safety shield 54.

Interior regions of locking collar 76 near proximal end 78 define barbs 90 preferably having a tapered proximal face 92 and a radially aligned distal face 94. Faces 92 and 94 of barbs 90 intersect to define an inside diameter "l" which is slightly greater than outside diameter "c" in groove 32 on luer collar 28 but less than outside diameter "b" at other locations on luer collar 28. Locking collar 76 is further defined by a plurality of slots 96 extending distally from proximal end 78. Shield 54 preferably includes a distal cover 98 securely mounted over distal end 58. Cover 98 includes a central aperture through which needle assembly 40 may extend. The aperture in cover 98 is dimensioned to prevent insertion of a finger.

Figure 7:
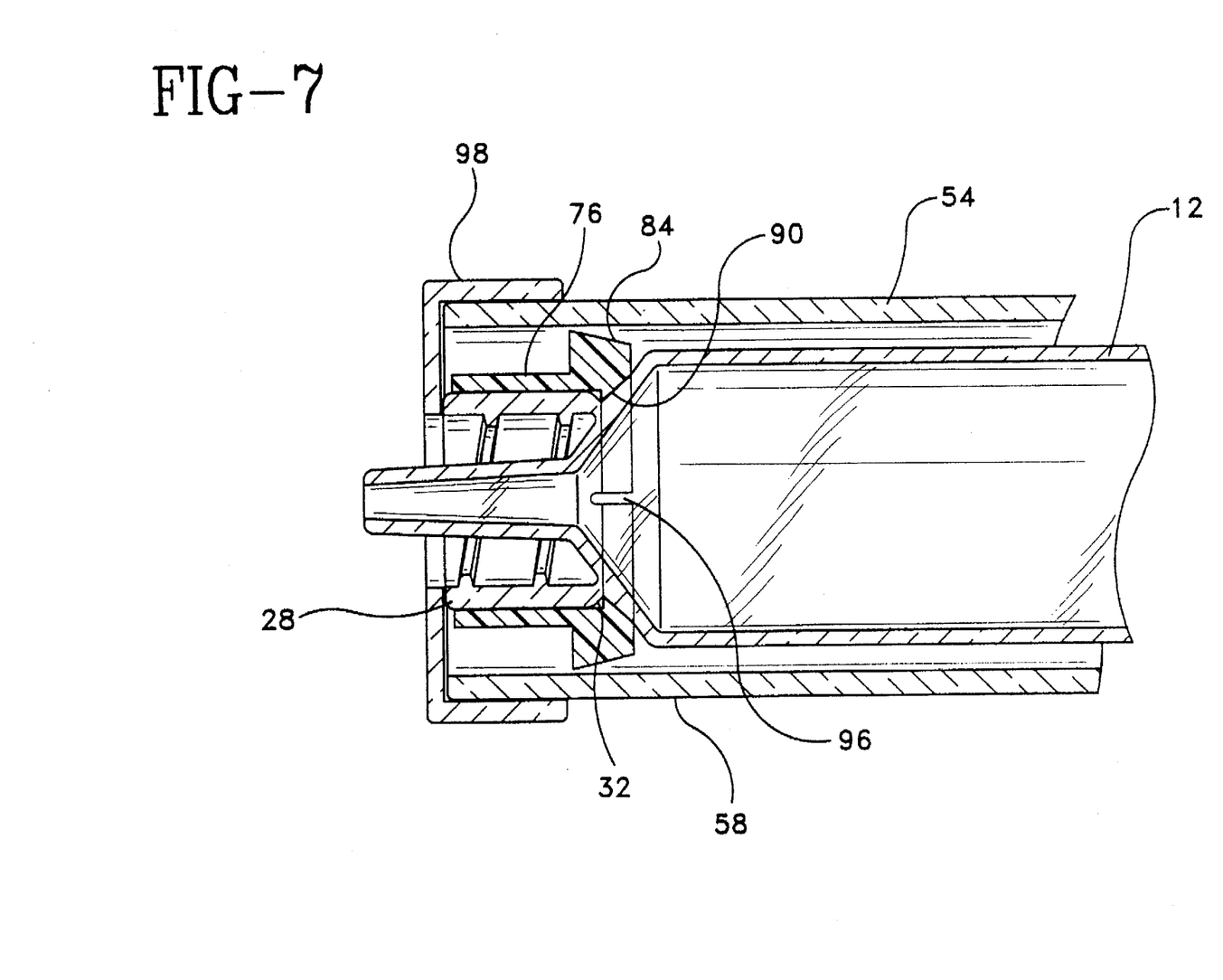
FIG. 7 is a cross-sectional view similar to FIG. 3 showing the safety shield assembly mounted on the hypodermic syringe and in the ready to use condition of the hypodermic syringe.

Shieldable syringe assembly 10 may be assembled by initially mounting shield 50 over syringe barrel 12. The outside diameter of syringe barrel 12 adjacent proximal end 16 may be formed slightly larger than the outside diameter of the remainder of the barrel so that the proximal end of the barrel may releasably frictionally engage locking shoulder 62 for holding shield 54 in its proximal position on syringe barrel 12. Locking collar 76 may then be slidably advanced into distal end 58 of safety shield 54 and over luer collar 28. During this insertion, ramped proximal face 92 of barbs 90 will engage luer collar 28, thereby causing portions of locking collar 76 adjacent slots 96 to radially expand. This radial expansion permits further proximal movement of locking collar 76 over luer collar 28. After sufficient proximal movement, however, barbs 90 will align with groove 32 of luer collar 28. Thus, proximal end 78 of locking collar 76 will resiliently return toward an undeflected condition, with barbs 90 securely engaged in groove 32 as shown in FIG. 7. Assembly may be completed by securely mounting cover 98 over distal end 58 of safety shield 54 and by threadedly engaging projections 50 of needle hub 48 into luer collar 28.

Shieldable needle assembly 10 may be used in a conventional manner by merely removing cap 52 from needle cannula 42 and hub 48. Hypodermic syringe 10 may then be filled in the conventional manner and used to inject an appropriate medication into a patient.

Figure 8:
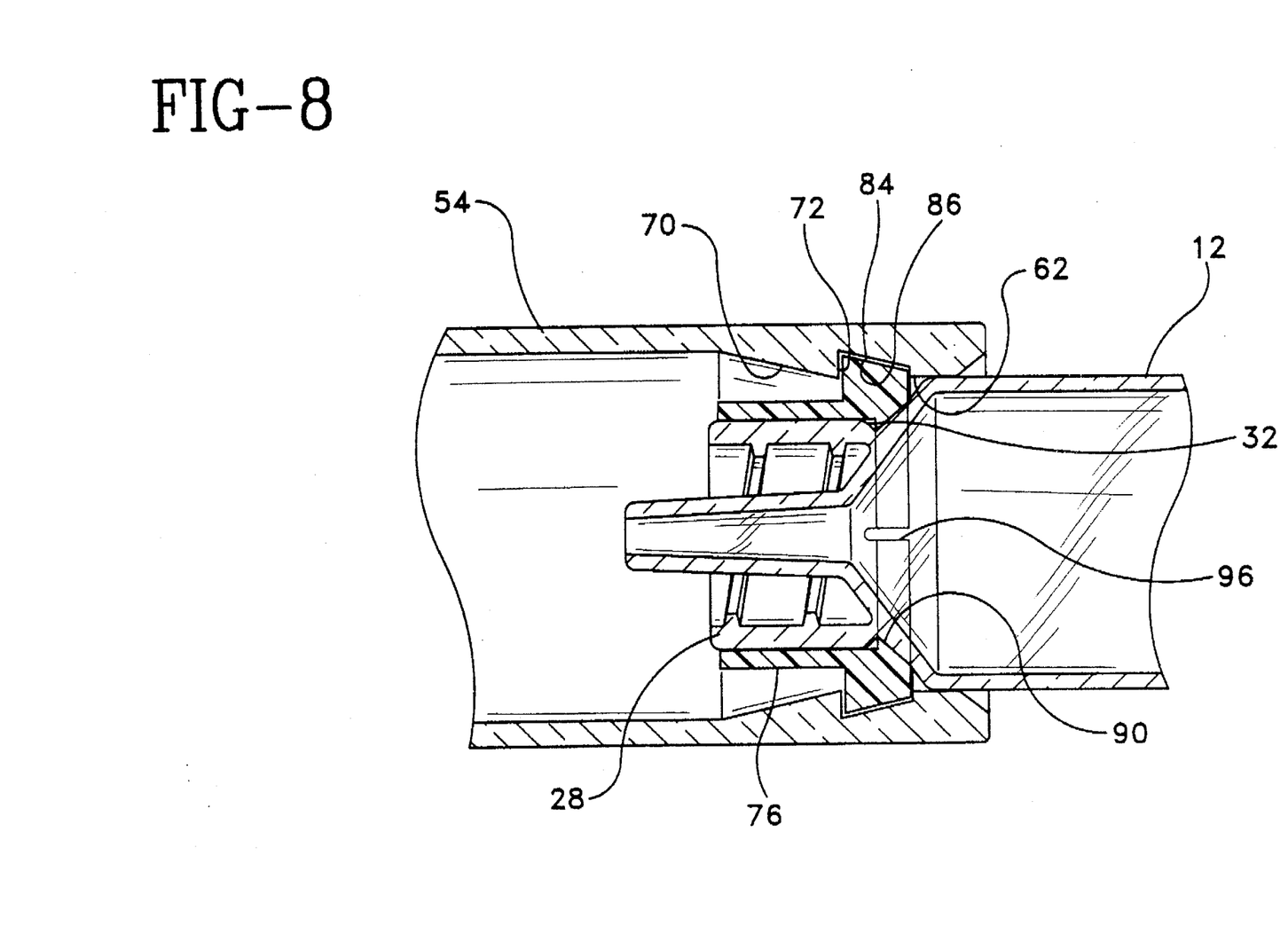
FIG. 8 is a cross-sectional view similar to FIG. 7, but showing the safety shield locked in its shielding position on the hypodermic syringe.

After such use, needle cannula 42 may be contaminated. To prevent accidental sticks with used needle cannula 42 and to prevent unauthorized reuse of hypodermic syringe 10, the technician using syringe 10 merely urges safety shield 54 distally relative to syringe barrel 12. Initial distal forces on safety shield 54 will disengage locking shoulder 62 from its frictional engagement with slightly enlarged portions at proximal end of syringe barrel 12. Further distal movement will proceed without substantial interference. However, as safety shield 54 completes its surrounding engagement with needle cannula 42, ramp faces 74 of pawls 70 will engage frustum-shaped wedge face 86 of exterior wedge 84 on locking collar 76. This initial engagement will generate a slight radial expansion of portions of safety shield 54 near proximal end 56 to permit further distal movement of locking shield 54. However, after further distal movement of locking shield 54, wedge surface 68 thereof will align with exterior wedge 84 on locking collar 76, thereby permitting proximal portions of safety shield 54 to resiliently contract into a preferably unexpanded condition as shown in FIG. 8. Slightly further distal movement of safety shield 54 will cause the smaller proximal end of wedge surface 68 to enter into wedged engagement with exterior wedge 84 on locking collar 76. This engagement will slow further distal movement of safety shield 54 and will simultaneously urge barbs 90 on the interior of locking collar 76 into tighter gripping engagement in groove 32 of luer collar 28. When using normal operating forces, additional distal movement is prevented by engagement of locking face 66 of locking shoulder 62 with proximal end 78 of locking collar 76 and by tighter wedged engagement between wedge surface 68 on safety shield 54 and exterior wedge 84 on locking collar 76. Again, when using normal operating forces, movement or removal of locking collar 76 relative to luer collar 28 is prevented by inwardly directed forces on barbs 90 caused by the above described wedging interaction between safety shield 54 and locking collar 76. Additionally, the minor diameter intersection of surfaces 92 and 94 of barbs 90 will be urged into tight gripping engagement with the frustum-shaped face 36 of groove 32 on luer collar 28. As a result, removal of safety shield 56 in a distal direction is positively prevented by these interactions, and attempts to effect removal function to increase the resistance against removal.

A return or proximal movement of safety shield 54 also is prevented. In particular, pawl face 72 of pawl 70 on safety shield 54 will be urged into radially aligned face 88 of exterior wedge 84 on locking collar 76. Proximally directed forces will then merely urge proximal end 78 of locking collar 76 against shoulder 30 at the interface of cylindrical side wall 18 of syringe barrel 12 and luer collar 28. Thus, the re-exposure of used needle cannula 42 also is positively prevented.

While the invention has been described with respect to a preferred embodiment, it is apparent that changes can be made without departing from the scope of the invention as defined herein. For example, other arrangements for releasably holding the safety shield in its retracted ready to use condition, such as mechanical interaction between the elements, may be provided. Additionally, the interior surface of the safety shield near the proximal end may be provided with one continuous circumferential locking shoulder and one continuous circumferential pawl or with a plurality of circumferentially spaced locking shoulders and pawls achieving the same function. Similarly, the exterior wedge on the locking collar and the barb on the locking collar may be circumferentially continuous or circumferentially discontinuous.

I claim:

1. A shieldable syringe assembly comprising:
a syringe barrel having a proximal end and a distal end, an inwardly directed groove formed on said syringe barrel;
a locking collar mounted around said syringe barrel, said locking collar including an inwardly deformable collet, a portion of said collet extending into said groove; and
a tubular safety shield telescoped over said syringe barrel and over said locking collar and being movable from a proximal position on said syringe barrel to a distal position, collet engaging means being formed on said safety shield for lockingly engaging said collet when said safety shield is in said distal position and for deforming said collet inwardly into tight engagement in said groove of said syringe barrel for preventing further movement of said safety shield from said distal position.

2. The assembly of claim 1, wherein said locking collar is generally tubular and includes opposed proximal and distal ends, said collet being substantially adjacent said proximal end of said locking collar.

3. The assembly of claim 2, wherein said collet of locking collar includes a plurality of slots extending distally from said proximal end for facilitating inward deformation of said collet.

4. The assembly of claim 3, wherein said collet includes a substantially frustum shaped exterior.

5. The assembly of claim 4, wherein said collet engaging means of said safety shield includes a substantially frustum shaped interior surface region substantially adjacent said proximal end of said safety shield for wedged engagement with said collet and for deforming said collet inwardly on said syringe barrel.

6. The assembly of claim 4, wherein said collet engaging means on said safety shield includes at least one stop block projecting inwardly on said safety shield adjacent said proximal end, said stop block defining a cross-sectional dimension smaller than said collet of said locking collar, such that said stop block prevents movement of said safety shield distally beyond said locking collar.

7. The assembly of claim 4, wherein said collet engaging means of said safety shield includes at least one inwardly directed pawl having a proximal ramp face and a distal pawl face, said pawl face being aligned and dimensioned for lockingly engaging a distal portion of said collet for preventing proximal movement of said safety shield from said distal position.

8. The assembly of claim 1, wherein said syringe barrel includes a generally tubular side wall and a luer collar projecting distally from said tubular side wall, said luer collar being cross-sectionally smaller than said side wall such that a generally annular shoulder extends between said luer collar and said tubular side wall, said groove being formed in said luer collar.

9. The assembly of claim 8, wherein said locking collar includes a proximal end engaged against said shoulder of said syringe barrel for preventing movement of said locking collar proximally from said luer collar.

10. A shieldable syringe assembly comprising:
a syringe barrel having a cylindrical side wall a proximal end and a distal end, an annular shoulder extending inwardly at said distal end of said side wall, a luer collar projecting distally from said shoulder, an inwardly formed groove on portions of said luer collar substantially adjacent said shoulder;
a locking collar mounted around said luer collar and including opposed proximal and distal ends, said proximal end of said locking collar defining a collet having an inner surface extending into said groove of said luer collar; and a frustum-shaped outer surface with a minor diameter adjacent said proximal end and a major diameter distally from said proximal end, said minor diameter end of said collet projecting outwardly beyond said side wall of said syringe barrel; and
a rigid tubular safety shield having proximal and distal ends, said safety shield being telescoped over said syringe barrel and over said locking collar and being slidably movable from a proximal position on said syringe barrel to a distal position, interior surface regions of said safety shield adjacent said proximal end defining a wedge surface for wedged engagement with said collet when said safety shield is in said distal position, at least one pawl distally of said wedge surface for locked engagement with said collet, whereby said pawl resists proximal movement of said safety shield from said distal position and whereby said wedge surface of said safety shield resists distal movement of said safety shield from said distal position.

11. The assembly of claim 10 wherein said collet includes a plurality of distally extending slots.

* * * * *